United States Patent [19]

Weathers

[11] Patent Number: 5,219,322

[45] Date of Patent: Jun. 15, 1993

[54] PSYCHOTHERAPY APPARATUS AND METHOD FOR TREATING UNDESIRABLE EMOTIONAL AROUSAL OF A PATIENT

[76] Inventor: Lawrence R. Weathers, West 1525 - 8th Ave., Spokane, Wash. 99204

[21] Appl. No.: 891,696

[22] Filed: Jun. 1, 1992

[51] Int. Cl.$^5$ ............................................. A61M 21/00
[52] U.S. Cl. .......................................................... 600/27
[58] Field of Search ...................................... 600/26–28

[56] References Cited

U.S. PATENT DOCUMENTS

| | | | |
|---|---|---|---|
| 3,826,250 | 7/1974 | Adams | 600/28 |
| 4,140,997 | 2/1979 | Brady | 128/732 |
| 4,282,864 | 8/1981 | Pizer | 600/27 |
| 4,289,121 | 9/1981 | Kupriyanovich | 600/27 |
| 4,354,505 | 10/1982 | Shiga | 128/732 |
| 4,388,918 | 6/1983 | Filley | 600/27 |
| 4,640,266 | 2/1987 | Levy | 600/27 |
| 4,665,926 | 5/1987 | Leuner et al. | 600/26 |
| 4,777,937 | 10/1988 | Rush et al. | 600/27 |
| 4,902,274 | 2/1990 | Gleeson, III | 600/27 |
| 5,036,858 | 8/1991 | Carter et al. | 128/732 |

FOREIGN PATENT DOCUMENTS

| | | | |
|---|---|---|---|
| 0888601 | 9/1953 | Fed. Rep. of Germany | 600/27 |
| 3447105 | 7/1985 | Fed. Rep. of Germany | 600/27 |

Primary Examiner—Lee S. Cohen
Assistant Examiner—John P. Lacyk
Attorney, Agent, or Firm—John R. Flanagan

[57] ABSTRACT

A psychotherapy apparatus and method provides treating of an undesirable emotional arousal of a patient through coordinated and controlled presentation of visual and auditory stimuli to the patient. The operative steps of the psychotherapy apparatus and method include presenting visual stimuli observable by a stationarily-positioned patient at right and left extremes of the patient's range of lateral eye movement, alternately switching the visual stimuli laterally between the right and left extremes of the patient's range of lateral eye movement, presenting auditory stimuli to the patient's ears, alternately switching the auditory stimuli between the patient's ears synchronously with alternately switching of the visual stimuli between the right and left extremes of the patient's range of lateral eye movement, monitoring physiological responses of the patient to the visual and auditory stimuli, and, in response to such monitoring, controlling the presenting and switching of the visual and auditory stimuli so as to elicit a mental imagery of a negative experience of the patient and to eliminate the undesirable emotional arousal evoked by the negative experience and to substitute a positive experience reinforcing a desired new behavior.

26 Claims, 2 Drawing Sheets

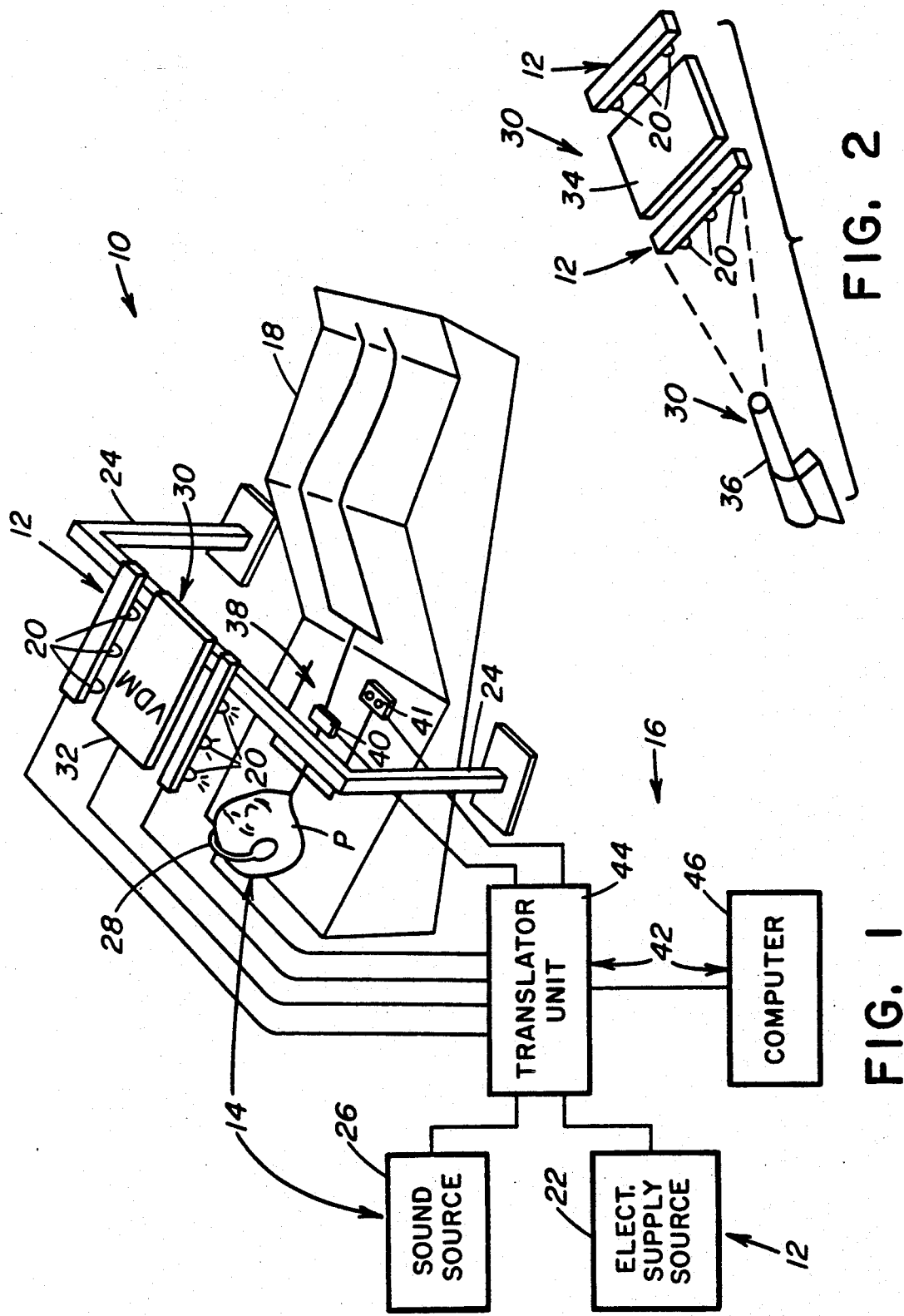

PSYCHOTHERAPY APPARATUS AND METHOD FOR TREATING UNDESIRABLE EMOTIONAL AROUSAL OF A PATIENT

BACKGROUND OF THE INVENTION

1. Field of the Invention

The present invention generally relates to psychotherapy techniques for treating emotional problems and, more particularly, to a psychotherapy apparatus and method for treating undesirable emotional arousal of a patient.

2. Description of the Prior Art

Many members of society currently demonstrating various undesirable (both pathological and non-pathological) behaviors are burdened with various emotional problems and emotionally-aggravated physical problems. Some examples of these problems are anxiety disorders, asthma, panic attacks, depression, anger, impotence, fears and phobias, grief, headaches, marriage problems, post Electro-Convulsive Therapy confusion, anxiety and memory loss, and post traumatic stress disorder (Vietnam and police service and child abuse and incest). The current undesirable behavior of a person provides connection of a current experience with a historical or more recent negative experience.

Heretofore, the primary mode of conducting psychotherapy for treatment of these problems has been by the use of one therapist with one patient or one or more therapists with a small group of patients. This mode of psychotherapy has been carried out mainly through verbal communication between therapists and patients. A significant drawback of relying primarily on verbal communication to conduct psychotherapy is that a large number of treatment sessions are needed to adequately deal with these problems. An unfortunate consequence of this is that the greater the overall quantity of time consumed in treatment the greater the cost and the fewer the number of persons that can be treated by a given population of therapists with proper qualification and clinical training. Another significant drawback is that some adults and many children are not verbal enough to successfully profit from verbal therapies.

Consequently, a need exists for a different approach to psychotherapy for treatment of emotional problems and emotionally-aggravated physical problems which approach will overcome the above-described drawbacks without introducing new ones in their place.

SUMMARY OF THE INVENTION

The present invention provides a psychotherapy apparatus and method being designed to satisfy the aforementioned needs. The psychotherapy apparatus and method of the present invention employ a sequence of operative steps which preferably are conducted in an automated manner so as to thereby reduce the number of treatment sessions and increase the number of patients that can be handled by a given therapist. The apparatus and method are designed for treating an undesirable emotional arousal of a patient through coordinated presentation of visual and auditory stimuli to the patient and through control of the visual and auditory stimuli. Preferably, although not necessarily, the visual and auditory stimuli is controlled in response to monitoring and measuring the physiological responses of the patient to the visual and auditory stimuli.

Accordingly, the present invention is directed to a psychotherapy apparatus for treating an undesirable emotional arousal of a patient. The psychotherapy apparatus basically comprises: means for presenting visual stimuli so as to be observable by a stationarily-positioned patient substantially at predetermined opposite extremes of the patient's range of eye movement; means for presenting auditory stimuli to the ears of the patient; and control means connected to the visual stimuli presenting means and to the auditory stimuli presenting means for operating the visual stimuli presenting means to alternately switch the visual stimuli between the predetermined extremes of the patient's range of eye movement and for operating the auditory stimuli presenting means to alternately switch the auditory stimuli between the patient's ears. The control means is capable of operating the visual stimuli presenting means and the auditory stimuli presenting means to cause alternate switching of the visual stimuli and auditory stimuli in a predetermined coordinated synchronous relationship with respect to one another so as to elict in the patient a mental imagery of a given past negative experience of the patient and to eliminate the undesirable emotional arousal evoked in the patient by the given negative experience and to substitute a positive experience reinforcing a desired new behavior.

More particularly, the predetermined extremes are right and left lateral extremes of the patient's lateral eye movement. The visual stimuli presenting means includes a bank of lights located at each of the right and left lateral extremes of the patient's eye movement. The control means is operable to alternately blink the lights individually back and forth between the predetermined extremes of the patient's eye movement.

The auditory stimuli presenting means includes means for generating a sound and a pair of stereo headphones capable of being worn over the ears of the patient. The headphones are operable for receiving the sound and transmitting the sound to the patient's ears. The control means is connected between the headphones and the sound generating means and is operable to alternately switch the sound being transmitted through the headphones back and forth between the patient's ears.

The psychotherapy apparatus also comprises means disposed between the predetermined extemes of the patient's range of eye movement for displaying visual information toward the stationarily-positioned patient. The displaying means includes a video display monitor disposed between the predetermined extremes of the patient's range of eye movement. The control means is connected to the displaying means and is operable to cause the displaying means to display the visual information in a predetermined pattern.

Further, the control means includes means for monitoring and measuring at least one predetermined physiological response of the patient to the visual and auditory stimuli and producing an output representative of the response. The control means also includes means connected to the monitoring and measuring means for receiving the output thereof and for controlling, in response to the output, the visual stimuli presenting means and the auditory stimuli presenting means.

Also, the present invention is directed to a psychotherapy method for treating an undesirable emotional arousal of a patient. The psychotherapy method basically comprises the steps of: presenting visual stimuli so as to be observable by a stationarily-positioned patient substantially at predetermined opposite extremes of the patient's range of eye movement; presenting auditory stimuli to the ears of the patient; alternately switching the visual stimuli between the predetermined extremes of the patient's range of eye movement; and alternately switching the auditory stimuli between the patient's ears so as to elict in the patient a mental imagery of a given negative experience of the patient and to eliminate the undesirable emotional arousal evoked in the patient by the given negative experience and to substitute a positive experience reinforcing a desired new behavior.

The psychotherapy method further comprises the steps of: monitoring and measuring a predetermined physiological response of the patient to the visual and auditory stimuli; and controlling, in response to the monitoring and measuring of the patient's physiological responses, the presenting and alternating of the visual and auditory stimuli.

These and other features and advantages of the present invention will become apparent to those skilled in the art upon a reading of the following detailed description when taken in conjunction with the drawings wherein there is shown and described illustrative embodiments of the invention.

BRIEF DESCRIPTION OF THE DRAWINGS

In the following detailed description, reference will be made to the attached drawings in which:

FIG. 1 is a diagrammatic view of a preferred embodiment of a psychotherapy apparatus of the present invention.

FIG. 2 is a partial diagrammatic view of a modified embodiment of the psychotherapy apparatus of FIG. 1.

DETAILED DESCRIPTION OF THE INVENTION

Figure 3:
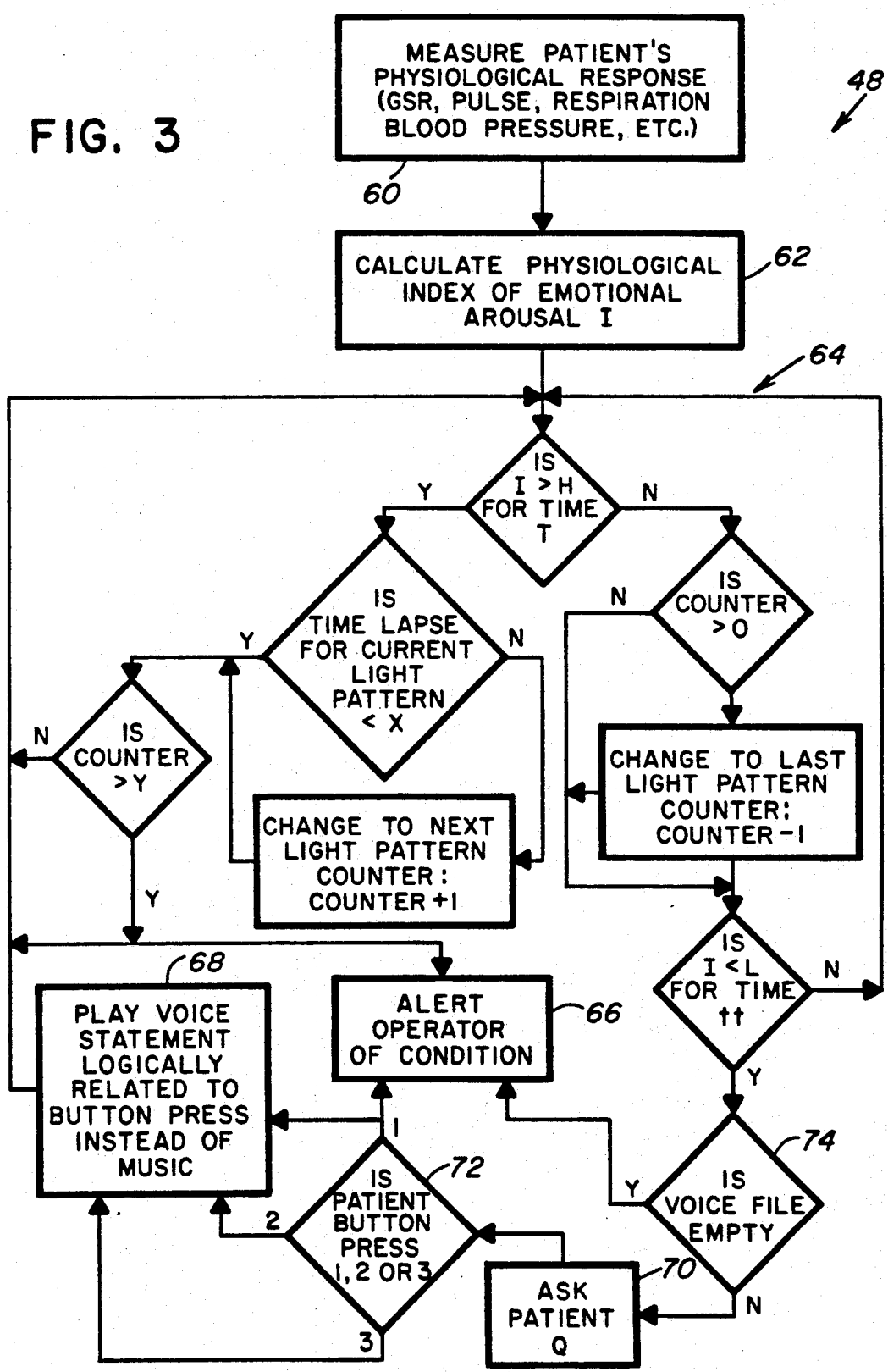
FIG. 3 is a flow chart of a preferred embodiment of a portion of a software program stored and executed by a computer of the psychotherapy apparatus of FIG. 1.

Referring to FIG. 1, there is illustrated a preferred embodiment of a psychotherapy apparatus of the present invention, generally designated 10, for carrying out a preferred embodiment of a psychotherapy method of the present invention. Overall, the psychotherapy apparatus 10 is designed for treating an undesirable emotional arousal of a patient P. In accordance with the psychotherapy apparatus 10 of the present invention, the treatment of emotional arousal is provided through a coordinated and controlled sequence of presentations of visual and auditory stimuli to the patient P in response to monitoring and measuring of at least one physiological response of the patient to the visual and auditory stimuli. The coordinated and controlled sequence is designed to elict in the patient a mental imagery of a given traumatic or negative experience of the patient and to eliminate the undesirable emotional arousal evoked in the patient by the given negative experience and to substitute a positive experience reinforcing a new desired behavior.

Referring to FIG. 1, the psychotherapy apparatus 10 basically includes means 12 for presenting visual stimuli, means 14 for presenting auditory stimuli, and control means 16 connected to the visual stimuli presenting means 12 and to the auditory stimuli presenting means 14. With respect to a patient P disposed in a stationary position, the visual stimuli presenting means 14 is located so as to be capable of observation approximately near or at predetermined opposite limits or extremes of the patient's range of eye movement. The preferred predetermined opposite limits or extremes are the right and left extremes of the patient's range of lateral eye movement. The auditory stimuli presenting means 14 is capable of providing the auditory stimuli to the ears of the patient P. The control means 16 is capable of operating the visual stimuli presenting means 12 to alternate the visual stimuli between predetermined extremes of the patient's range of eye movement. Also, the control means 16 is capable of operating the auditory stimuli presenting means 14 to alternate the auditory stimuli between the patient's ears. Further, the control means 16 is capable of operating the visual stimuli presenting means 12 and the auditory stimuli presenting means 14 in a predetermined synchronized alternating relationship with respect to one another.

In a practical implementation of the psychotherapy apparatus 10 as diagrammatically depicted in FIG. 1, the patient P is disposed in the stationary position on a suitable support structure 18, one example of which can be a reclining chair. The visual stimuli presenting means 12 includes means for generating light such as a pair of right and left pluralities or banks of lights 20 and a source 22 capable of providing a supply of electrical power to the banks of lights 20. Also, the visual stimuli presenting means 12 includes means for positioning the lights such as a pair of right and left upright support stands 24 which support the banks of lights 20 at the right and left extremes of the patient's range of lateral eye movement. Preferably, the banks of lights 20 are respectively pluralities of light-emitting diodes (LEDs), such as three lights being arranged in each of the respective rows lying in generally vertical planes which are laterally displaced from and generally parallel to one another. Other types of lights or moving objects can be equally utilized.

The control means 16 is capable of switching or moving the visual stimuli in alternating fashion between the right and left extremes of the patient's range of lateral eye movement. The visual stimuli is switched or moved by alternately blinking the lights 20 of the right and left banks thereof, back and forth either laterally or alternatively diagonally across from one another, between the right and left extremes of the patient's range of lateral eye movement. Also, the control means 16 is operable to cause alternate blinking of the lights 20 back and forth at different speeds, for example, ranging between thirty and sixty cycles per minute.

Also, in the one practical implementation of the psychotherapy apparatus 10 diagrammatically depicted in FIG. 1, the auditory stimuli presenting means 14 includes a source 26 for generating a pre-recorded sound and a pair of stereo headphones 28 connected to the sound source 26 and capable of being worn over the ears of the patient P. By way of example, the sound source 26 can be an audio cassette player operable to play an audio cassette tape containing the pre-recorded sound, such as music and verbal messages. Additionally, the sound source 26 can include a microphone to permit overlaying of speech messages on the music so that the speech will be interspersed with the music. The pre-recorded and/or live sounds generated from the sound source 26 are transmitted to the patient's ears through the separate channels of the stereo headphones 28 worn by the patient P. The control means 16 is capable of moving the auditory stimuli between the patient's ears in alternating fashion by switching the pre-recorded sound transmitted through the channels of the stereo headphones 36 back and forth between the patient's ears.

Further, in the one practical implementation diagrammatically depicted in FIG. 1, as an optional but preferred feature, the psychotherapy apparatus 10 includes means 30 disposed between the right and left extemes of the patient's range of lateral eye movement for displaying visual information toward the stationarily-positioned patient P such that the information is readily observable by the patient. Preferably, the displaying means 30 is a video display monitor 32 supported between the right and left extremes of the patient's range of eye movement by the pair of support stands 24. The control means 16 is connected to the video display monitor 32 and is operable to cause the display monitor 32 to display the visual information in a desired predetermined pattern. Referring to FIG. 2, there is illustrated a modified embodiment of the psychotherapy apparatus 10 in which, instead of the video display monitor 32 of FIG. 1, the displaying means 30 includes a screen 34 disposed between the banks of lights 20 and a projector 36, such as a tachistoscope, operable for projecting a display of information in the desired predetermined pattern on the screen 34.

Also, in the one practical implementation of the psychotherapy apparatus diagrammatically depicted in FIG. 1, the control means 16 includes means 38 for monitoring and measuring at least one and preferably a plurality of predetermined physiological responses of the patient P to the visual and auditory stimuli and producing an output representative of the response. The monitoring and measuring means 38 includes a plurality of detectors 40 for continuously sensing various of the patient's physiological responses and producing corresponding outputs which are representative of the sensed responses. As examples, various of the patient's physiological responses which are advantageously monitored and measured electronically are pulse, Galvanic Skin Response (GSR) and respiration rate. The monitoring and measuring means 38 also includes a plurality of buttons 41 which permit the patient to respond to questions directed to the patient either verbally through the headphones 28 by the operator or visually via the video display monitor 32 or screen 34.

The control means 16 also includes an arrangement 42 connected to the monitoring and measuring means 38 and connected to the visual and auditory stimuli presenting means 12, 14 and to the visual information displaying means 30 and being operable for receiving the output of the monitoring and measuring means 38 and for controlling, in response to such output, the visual and auditory stimuli presenting means 12, 14 and the visual information displaying means 30 so as to elicit in the patient a mental imagery of a given negative experience of the patient and to eliminate the undesirable emotional arousal evoked in the patient by the given negative experience and to substitute a positive experience reinforcing a desired new behavior. More particularly, the arrangement 42 includes a translator unit 44, a digital computer 46, and a software program 48 stored in the digital computer 46. Only the portion of the software 48 that automatically controls the lights and sounds in response to the measured physiological responses from the patient and to the buttons 41 activated by the patient is outlined by the detailed flow chart in FIG. 3.

The translator unit 44 is connected to the detectors 40 and buttons 41 of the monitoring and measuring means 38 for receiving the outputs thereof and producing translated outputs corresponding thereto. The translator unit 44 also is connected to the visual stimuli presenting means 12, the auditory stimuli presenting means 14 and the visual information displaying means 30. The computer 46 and software 48, via the translator unit 44, are capable of operating the banks of lights 20 of the visual stimuli presenting means 12 to blink and move the light in alternating fashion between the right and left extremes of the patient's range of lateral eye movement as described above. The computer 46 and software 48, via the translator unit 44, are also capable of operating the sound source 26 and headphones 28 of the auditory stimuli presenting means 14 to cause moving of the sound generated by the source 26 and received by the headphones 28 between the patient's ears in alternating fashion and synchronous relation with the light. The translator unit 44 is made up primarily of any suitable interconnection of conventional electronic components operable to convert analog signals produced and employed by the visual and auditory stimuli presenting means 12, 14, information displaying means 30, and monitoring and measuring means 38, to digital signals produced and employed by the computer 46, and vice versa, and thus need not be illustrated nor described in detail.

The digital computer 46 is connected to the translator unit 44 and receives signals therefrom and sends signals thereto. The computer 46 is operable, in response to input signals via the translator unit 44, to run the software program 48 and produce output signals via the translator unit 44 to control operation of the visual and auditory stimuli presenting means 12, 14 and of the visual information displaying means 30. As an example, the digital computer 46 can be a 386/33 AT personal computer. The software program is preferably written in C programming code.

Referring to FIG. 3, there is illustrated a flow chart of a preferred embodiment of the portion of the software program 48 that automatically controls the lights and sounds in response to physiological measures which is stored and executed by the digital computer 46 of the psychotherapy apparatus 10. The terms (dynamic variables) used in the program flow chart 48 are defined TABLE I as follows:

| TABLE I | |
|---|---|
| I = | Computed index of physiologically measured emotional arousal. |
| H = | Highest desirable level of I. |
| T = | The amount of time during which I must be greater than H before corrective action is taken. |
| L = | Level of I where there is nominal emotional arousal. |
| tt = | The amount of time during which I must be less than H before a voice segment is played. |
| Y = | The maximum number of new light patterns the apparatus may try before the operator is notified. |
| X = | The minimum time/repetitions each light pattern runs before the apparatus may be moved to the next pattern. |
| Counter = | Keeps track of how many new light patterns have been tried to reduce emotional arousal I to below H. |

Clinical experience in operating the psychotherapy apparatus 10 indicates that the most important operator activities are (1) to monitor nervous system arousal and ask questions or give instructions to the patient when emotional arousal is at its lowest points and (2) to increase the complexity of the light patterns, to dilute the intensity of the internal imagery, when the sympathetic nervous system arousal is too high. By electronically monitoring the patient's pulse, GSR and repiration rate, for example, the apparatus 10 is automated such that timely control of the visual and auditory stimuli can readily achieved. The outputs received from detectors 40 monitoring of the patient's various physiological responses and translated by the translator unit 44 are fed to the digital computer 46 and the index of emotional arousal I is computed by the software program 48 that is maximally sensitive to the level of mobilization, e.g., emotional arousal, of the sympathetic nervous system.

The monitoring and measuring of the changes in the patient's physiological responses is represented by block 60 of the program flow chart 48, whereas the calculation of the index of emotional arousal I is represented by block 62 of the program flow chart. The emotional arousal index I is constantly changing in view that the patient's physiological responses being monitored are constantly changing. The emotional arousal index I is fed into a logic loop 64 of the program 48 which includes series of decision points and paths where it is continuously compared to other variables identified in TABLE I above in order to assess its level and thereby to determine the level of mobilization of the sympathetic nervous system at any given time.

The index I is used to change the light patterns when arousal exceeds maximum desirable value of variable H for time T. A momentary spike of I above H is presently thought to be meaningless and will have no effect on the light patterns. The program 48 allows the apparatus 10 to try more complex light patterns Y times before the operator is alerted, as per block 66 of the logic loop 64 of the flow chart 48. Each light pattern is displayed to the patient as least X times before it is allowed to be changed. Increasing the speed and thus the complexity of the light patterns is a way to reduce the emotional arousal index I since the patient will devote more attention to the light pattern itself and corresponding divert attention away from the internal imagery which is causing the excessive arousal. Thus, the increased complexity of the light patterns dilutes the patient's experience of the arousing imagery and therefore reduces the arousal index I. The counter value Y is returned to zero when I decreases to less than the maximum value of the variable H.

If more complex light patterns have been used, once the index I is below maximum value of H for T time, the complexity of the light patterns is reduced in a stepwise fashion until the patient is returned to the basic light pattern. The stepup and stepdown rates may be different. The size of the steps may also be different.

Conversely, when the arousal index I is indicative of nominal emotional arousal for a meaningful period of time, less than L for time tt, a PC sound digitizing board of the sound source 30 is used to overlay pre-recorded questions and instructions, as per block 68 of the flow chart logic loop 64, over the music the patient is hearing. First, a question is posed, as per block 70. Typically, the question focuses on whether the patient is having any emotional response to the current topic (in case I is not an accurate measure of emotional arousal for this subject), or whether the patient has spontaneously branched to a new topic. The response to this question provides the operator with an opportunity to take over manual control of the apparatus 10 to provide the patient with new direction.

The patient responds to the question by pressing one of several buttons 41, as per block 72 of flow chart logic loop 64. The patient presses one button for no emotional response, another button for some emotional response, and a third button if the patient has drifted to a new topic. If the last button is pressed, then the operator is notified, as per block 66.

Based on these button presses and values of I, a new instruction is selected from a data base and played to the patient. The logic loop 64 feedbacks to the initial comparison of arousal index I with maximum arousal value of variable H for time T. The instructions are stored digitally in logical units in a data base on the hard disc of the computer 46. It should be realized that there are different sequences of instructions employed for different treatment purposes. The operator is notified, as per block 74, when the computed file of voice prompts is empty. Voice files for common problems are standard and stored in a library on the hard disk. Voice files for unique individual problems can be quickly recorded to the hard drive.

In summary, the above-described features of the psychotherapy apparatus 10 of the present invention acting together provide for treatment of undesirable emotional arousal of a patient through a coordinated and controlled presentation of visual and auditory stimuli to the patient. The steps of the psychotherapy method of the present invention correspond to the above-described operations performed by the psychotherapy apparatus 10.

In accordance with the psychotherapy method of the present invention, a visual stimuli such as the lights 20 are blinked to cause movement of electromagnetic energy in the visible spectrum, i.e., ordinary light, back and forth laterally and/or diagonally between the opposite right and left extremes of the patient's range of lateral eye movement. The light is moved at speeds which permit the patient P, by merely using his or her eyes, to easily observe and follow the moving light. The effect of light movement and observation of it by the patient P is to produce a therapeutic altered state of consciousness in the patient P.

Also, in accordance with the psychotherapy method of the present invention, this effect on the patient P is substantially augmented by having the patient P listen to auditory stimuli, such as music and voice or verbal statements, through a pair of stereo headphones 28. The sound is switched back and forth between the right and left ears of the patient P so as to move the auditory stimuli between the ears synchronously with movement of the light. Further, in accordance with the psychotherapy method of the present invention, visual information in a desired predetermined pattern is displayed by a video display monitor 32 toward the stationarily-positioned patient from between the right and left extremes of the patient's range of lateral eye movement.

Still further, in accordance with the psychotherapy method of the present invention, physiological responses of the patient to the visual and auditory stimuli and visual display information are monitored and measured and, in response thereto, the visual and auditory stimuli and visual display information are controlled in a desired manner which is designed to elicit a mental imagery of a given negative experience of the patient and to reduce the undesirable emotional arousal evoked by the negative experience. The monitoring and measuring includes sensing the patient's physiological responses and producing outputs which represent the sensed responses. These outputs provide measures of the emotional arousal of the autonomic nervous system of the patient P.

The back and forth movement of the visual and auditory stimuli and displaying of the visual display information are controlled by operating the digital computer 46 storing the software program 48. In response to receipt of the outputs representative of the patient's physiological responses, the computer 46 executes or runs the software program 48 so as to produce output signals which control the visual and auditory stimuli and displayed information in the desired manner designed to elict the mental imagery of the given negative experience of the patient and to extinguish the undesirable emotional arousal evoked by the negative experience and to substitute a positive experience reinforcing a desired new behavior.

In conjunction with the visual and auditory stimuli controlled by the computer, the operator by using the microphone can direct the patient's attention through the following sequence in order to extinguish the negative experience and substitute a positive experience of the reinforcing stimulus related to the new behavior:

(1) Defining the undesirable behavior. Operator in collaboration with patient specifies, from patient's phenomenological perspective, what is the experience of undesireable behavior. An example might be over-eating high fat foods.

(2) Defining cue stimuli for the undesirable behavior. Operator specifies what internal or external stimuli trigger the undesirable behavior. With reference to the over-eating example, it might be that the sight of certain foods elicits autonomic responses such as salavation and feelings of hunger. Typically this results in almost automatic eating behavior.

(3) Extinguish cues for the undesirable behavior. Operator directs the patient to imagine and re-experience the triggering cues by vividly describing the experience of those cues and the sensations they elicit. With reference to the over-eating example, the patient is directed to remember the situations, feelings, etc., that usually preceed eating, such as sitting in front of the TV. The patient notes and continues to review the desire to eat that the cue elicits until that feeling fades away.

(4) Extinguish historical feelings linked to undesirable behavior. This involves extinguishing the underlying learning history for the undesirable behavior by following the feeling associated with the undesirable behavior back in time to previous times when that feeling was experienced, going all the way back to the first time the feeling was ever experienced. Stay with the feeling until it fades away. For instance, oftentimes eating certain foods is associated with past reinforcement or relief for discomfort. This association enhances the reinforcement value of the offending food.

(5) Extinguish undesirable behavior itself. Focus patient's attention on the unique feeling associated with the undesirable behavior, until the mind tends to wander and the patient has to apply volitional effort to continue to attend to the mental images. With reference to the over-eating example, have the patient skip a couple of meals before a treatment session so that the patient will feel very hungry. Then, during the session, have the patient focus on the hunger and the desire to eat until the sensation fades out.

(6) Define reinforcers for the undesirable behavior. Since a behavior is maintained by its consequences, it is important to identify these reinforcing consequences and extinguish their reinforcing value. Reinforcing stimuli follow the undesirable behavior. Social events often serve as reinforcers, though they may be a change in physiology, emotional arousal, perception, etc. With reference to the over-eating example, the reinforcers might be the taste, taking a break, socializing with friends, etc.

(7) Extinguish reinforcers for the undesirable behavior. Direct the patient to focus his or her attention on memories of the reinforcers until it does not elicit any feelings and becomes boring and takes effort to continue to focus. With reference to the over-eating example, have the patient focus on the texture, flavor, smell, and taste of the foods the patient should not eat. The effect is enhanced by having the patient actually nibble on favorite varieties of fattening foods during the session.

(8) Specify negative experience of undesirable behavior. From a phenomenological perspective of the patient, enumerate the negative experience of the undesirable behavior. With reference to the over-eating example, the negative experience might be that fat foods leave an oily taste in the mouth, and produce a sluggish feeling as they are digested.

(9) Attention to negative experience of undesirable behavior. Modify attentional patterns of the patient, by describing from the patient's phenomenology the undesirable experience of emitting the undesirable behavior, with particular focus of feelings and sensations. With reference to the over-eating example, repeatedly and colorfully describe to the patient, the gummy oily taste and feel characteristics of fatty foods.

(10) Specify negative self concept. Enumerate the physical, social, emotional and intellectual experiences that are part of the negative self concept. With reference to the over-eating example and the obesity which results, describe the undesirable physical look of the body, the inability to effectively participate in sports, health problems, not being able to wear attractive clothes, social rejection, disgust for self, etc.

(11) Extinguish negative self concept. Specificy in phenomenological language the negative view of self as related to the undesirable behavior. With reference to the over-eating example, the patient sees and feels himself or herself as the unappealing obese person he or she is. Go over this until all of the disgust and dislike of self becomes boring and is gone.

(12) Specificy what the triggering cues are that will elicit the new behavior. Specify what chaining cues the patient will need to attend to in order to initiate the new desirable behavior: internal sensations, feelings and thoughts or outside cues.

(13) Sensitize to triggering cues for the new behavior. Suggest that the patient imagine, feel, experience the cues specified to initiate the new behavior, being very attentive to the smallest details. Use language from the patient's phenomenological perspective. Provide deep relaxation instructions to enhance mental imagery, like sinking into a jacuzzi, warm waves of relaxation, sinking into a chair, a spring day in a mountain meadow, etc.

(14) Initiation of new behavior. Continue the deep relaxation instructions to enhance mental imagery. When the patient is profoundly relaxed, colorfully describe in detail the new behavior and all of its sensations, perceptions and experiences, clearly including the triggering cues.

(15) Specify the reinforcers for the new behavior. Specify what the reinforcers for the new behavior will be. The reinforcers to be described are usually social such as approving words, cues or actions by others.

(16) Attention to reinforcing positive experience of new behavior. In order to modify the attentional patterns of the patient, direct the patient's attention to the details of the phenomenological experience of the reinforcing stimuli related to the new behavior. With reference to the over-eating example, notice the subtle and delightful flavors of vegetables, breads and pasta.

(17) Specify new self concept. Enumerate the physical, social, emotional and intellectual experiences that are part of the positive self concept. With reference to the over-eating example and the resulting obesity, describe the attractive physical look of the body, the ability to effectively participate in sports, the condition of being healthy, of being able to wear attractive clothes, of social acceptance, of approving of self.

(18) Initiation of new self concept. Describe in detail the experience phenomenological experience of the new self concept. With reference to the over-eating example, the patient images looking at himself or herself in the mirror and admiring the attractive thin body, feeling how lively and athletic he or she is, or going to social events and seeing others admiring the patient's attractive look.

It should be mentioned that the therapeutic altered state of consciousness produced in the patient is similar to a state known as Rapid Eye Movement (REM) sleep, although unlike in REM sleep the patient is fully awake. However, the physiology of the patient approximates that of sleep and the patient has clear dream-like imagery that can be directed by the patient to issues of concern. The patient is asked to remember a specific undesirable, usually traumatic, event while watching the lights, for example, for 100 to 1000 cycles. The patient relives the event in the dream-like state. The effect of the treatment is that the memory of the event will remain but the affect is striped away so that recalling the event will no longer cause undesirable emotional arousal. When by either the physiological measurements or clinical observation of the physiology of the patient, the patient is no longer autonomically aroused, the therapy session directed to that particular traumatic event is concluded.

Furthermore, clinical evaluation of the psychotherapy method indicates that presenting the patient P with subliminal visual and auditory stimuli may accelerate this method of therapy. The state of consciousness produced by the psychotherapy apparatus and method of the present invention makes the patient more open to the effects of subliminal stimulation. The verbal subliminal portion of the auditory stimulation is embedded in the music that the patient listens to through the headphones 28. The visual information flashed on the screen of the video display monitor 32 spanning between the banks of lights 20 that the patient is watching is the subliminal portion of the visual stimulation. The computer 46 triggers the monitor 32 at the moment the light moves from one side of the patient P to other side. That is judged to be the time when the patient's eyes are tranversing the screen of the monitor 32 to receive the visual subliminal information flashed on the screen of the monitor 32.

It is thought that the present invention and its advantages will be understood from the foregoing description and it will be apparent that various changes may be made thereto without departing from its spirit and scope of the invention or sacrificing all of its material advantages, the form hereinbefore described being merely preferred or exemplary embodiment thereof.

Having thus described the invention, what is claimed is:

1. A psychotherapy apparatus for treating undesirable emotional arousal of a patient, comprising:
   (a) means for presenting visual stimuli so as to be observed by a stationarily-positioned patient substantially at predetermined opposite extremes of the patient's range of eye movement;
   (b) means for presenting auditory stimuli to the ears of the patient; and
   (c) control means connected to said visual stimuli presenting means and to said auditory stimuli presenting means for operating said visual stimuli presenting means to movably alternate the visual stimuli between the predetermined extremes of the patient's range of eye movement and for operating said auditory stimuli presenting means to movably alternate the auditory stimuli between the patient's ears.

2. The apparatus of claim 1 wherein said control means is for operating said visual stimuli presenting means and said auditory stimuli presenting means to move the visual stimuli and auditory stimuli in a predetermined coordinated synchronous relation with respect to one another.

3. The apparatus of claim 1 wherein said visual stimuli presenting means includes a bank of lights adapted to be located at each of said predetermined extremes of the patient's eye movement.

4. The apparatus of claim 3 wherein said control means is for operating said visual stimuli presenting means to alternately blink said lights of said banks back and forth between said predetermined extremes of the patient's eye movement.

5. The apparatus of claim 1 wherein said predetermined extremes are right and left lateral extremes of the patient's lateral eye movement.

6. The apparatus of claim 1 wherein said auditory stimuli presenting means includes:
   means for generating a sound; and
   a pair of headphones adapted to be worn over the ears of the patient, said headphones for operating to receive the sound and transmit the sound to the patient's ears.

7. The apparatus of claim 6 wherein said control means is connected between said sound generating means and said headphones and is for operating said sound generating means to alternately switch the sound being transmitted through said headphones back and forth between the patient's ears.

8. The apparatus of claim 1 further comprising:
   means disposed between said predetermined extremes of the patient's range of eye movement for displaying visual information toward the stationarily-positioned patient.

9. The apparatus of claim 8 wherein said control means is connected to said displaying means and is for operating to cause said displaying means to display the visual information in a predetermined pattern.

10. The apparatus of claim 8 wherein said displaying means includes a video display monitor adapted to be disposed between said predetermined extremes of the patient's range of eye movement.

11. The apparatus of claim 8 wherein said displaying means includes:

a screen adapted to be disposed between said predetermined extremes of the patient's range of eye movement; and a projector for operating said displaying means to project a display of information on said screen.

12. The apparatus of claim 1 wherein said control means includes means for monitoring and measuring at least one predetermined physiological response of the patient to the visual and auditory stimuli and producing an output representative of the response.

13. The apparatus of claim 12 wherein said monitoring and measuring means includes at least one detector for sensing the patient's physiological response and producing the output representative of the sensed response.

14. The apparatus of claim 12 wherein said control means further includes means connected to said monitoring and measuring means for receiving said output thereof and controlling, in response to said output, said visual stimuli presenting means and said auditory stimuli presenting means so as to elict in the patient a mental imagery of a given negative experience of the patient and to eliminate the undesirable emotional arousal evoked in the patient by the given negative experience and to substitute a positive experience reinforcing a desired new behavior.

15. The apparatus of claim 14 wherein said means for receiving and controlling includes a computer storing a software program and being operable, in response to said output of said monitoring and measuring means, to run said software program and provide output signals to control operation of said visual and auditory stimuli presenting means.

16. A psychotherapy method for treating an undesirable emotional arousal of a patient, comprising the steps of:

(a) presenting visual stimuli so as to be observed by a stationarily-positioned patient substantially at predetermined opposite extremes of the patient's range of eye movement;

(b) presenting auditory stimuli to the ears of the patient;

(c) alternately switching the visual stimuli between the predetermined extremes of the patient's range of eye movement; and (d) alternately switching the auditory stimuli between the patient's ears.

17. The method of claim 16 wherein said extremes are right and left lateral extremes of the patient's lateral eye movement.

18. The method of claim 16 wherein the visual stimuli and auditory stimuli are alternately switched in a predetermined coordinated synchronous relation with respect to one another.

19. The method of claim 16 wherein said presenting the visual stimuli includes generating light from a bank of lights located at each of said predetermined extremes of the patient's eye movement.

20. The method of claim 16 wherein said presenting the auditory stimuli includes generating a sound and transmitting the sound to the patient's ears through a pair of stereo headphones adapted to be worn over the patient's ears.

21. The method of claim 20 wherein said alternately switching the auditory stimuli includes alternately switching the sound from the stereo headphones back and forth between the patient's ears.

22. The method of claim 16 further comprising the step of:

displaying visual information toward the stationarily-positioned patient from between said predetermined extremes of the patient's range of eye movement.

23. The method of claim 16 further comprising the step of:

monitoring and measuring at least one predetermined physiological response of the patient to the visual and auditory stimuli and producing an output representative of the response.

24. The method of claim 23 wherein said monitoring and measuring includes sensing the patient's physiological response and producing the output representative of the sensed response.

25. The method of claim 23 further comprising the step of:

controlling said visual stimuli presenting and switching and said auditory stimuli presenting and switching, in response to the output representative of the patient's physiological response, so as to elict in the patient a mental imagery of a given negative experience of the patient and to eliminate the undesirable emotional arousal evoked in the patient by the given negative experience and to substitute a positive experience reinforcing a new desired behavior.

26. The method of claim 25 wherein said controlling includes operating a computer, in response to said output representative of the patient's physiological response, to run a software program stored in said computer so as to provide control of said presenting and alternating of the visual and auditory stimuli.

* * * * *